US00PP37577P2

(12) United States Plant Patent
Meilland

(10) Patent No.: US PP37,577 P2
(45) Date of Patent: Aug. 11, 2026

(54) BEDDING ROSE PLANT NAMED 'MEISAXA'

(50) Latin Name: *Rosa hybrida*
Varietal Denomination: MEISAXA

(71) Applicant: The Conard Pyle Company, West Grove, PA (US)

(72) Inventor: Alain Antoine Meilland, Antibes (FR)

(73) Assignee: The Conard Pyle Company, West Grove, PA (US)

( * ) Notice: Subject to any disclaimer, the term of this patent is extended or adjusted under 35 U.S.C. 154(b) by 0 days.

(21) Appl. No.: 19/434,713

(22) Filed: Dec. 29, 2025

(51) Int. Cl.
*A01H 5/02* (2018.01)
*A01H 6/74* (2018.01)

(52) U.S. Cl.
USPC ..... Plt./104

(58) Field of Classification Search
USPC ..... Plt./104, 134, 145
CPC . A01H 5/02; A01H 5/00; A01H 6/749; A01H 6/74
See application file for complete search history.

(56) References Cited

U.S. PATENT DOCUMENTS

PP21,467 P2 11/2010 Kordes
PP26,536 P3 * 3/2016 Olesen ..... A01H 5/02 Plt./145

OTHER PUBLICATIONS

CPVO Version 4.25.14 for Rosa Meisaxa, retrieved on Apr. 22, 2026 at https://online.plantvarieties.eu/publicConsultation Details?registerId=20260270&denomination=meisaxa, 2 pp. (Year: 2026).*

* cited by examiner

*Primary Examiner* — June Hwu
(74) *Attorney, Agent, or Firm* — Panitch Schwarze Belisario & Nadel LLP; Stephany G. Small; Travis W. Bliss

(57) ABSTRACT

A new and distinct variety of bedding rose plant, referred to by its cultivar name, 'MEISAXA', is described. The new plant variety forms in abundance on a nearly continuous basis, yellow-colored blossoms. The growth habit is bushy and compact. Dense, semi-glossy ornamental foliage is formed. Additionally, the new plant variety is particularly well suited for growing as ornamentation in the landscape.

1 Drawing Sheet

Latin name of genus and species of plant claimed: *Rosa hybrida.*

Variety denomination: 'MEISAXA'.

STATEMENT REGARDING PRIOR DISCLOSURES BY THE INVENTOR

The first sale or offer for of the new plant variety was Apr. 26, 2025 and first sale of the plant variety was May 15, 2025, in Japan. The first offer for sale of the new plant variety was by the inventor or another who obtained the new plant variety directly or indirectly from the inventor. No plants of the new plant variety have been sold in this country or anywhere in the world, nor has any disclosure of the new plant been made, more than one year prior to the effective filing date of this application, and such sale or disclosure within one year was either derived directly or indirectly from the inventor.

BACKGROUND OF THE INVENTION

The new variety of bedding rose plant of the present invention was created by controlled breeding during May 2015, in Le Cannet de Maures, Var, France by artificial pollination wherein two parents were crossed which previously had been studied in the hope that they would contribute the desired characteristics. The female parent (i.e., the seed parent) of the new plant variety was the 'KORgeleflo' variety (U.S. Plant Pat. No. 21,467). The male parent (i.e., the pollen parent) of the new plant variety was an unnamed seedling (not patented) that was the product of the cross between an unnamed seedling variety (not patented) and the 'HARkuly' variety (not patented).

The parentage of the new plant variety can be summarized as follows:

'KORgeleflo' x (unnamed seedling x 'HARkuly')

The seeds resulting from the above pollination were sown and small plants were obtained which were physically and biologically different from each other. Selective study resulted in the identification of a single plant of the new variety.

The new plant variety has been found to undergo asexual propagation in Le Cannet de Maures, Var, France by a number of routes such as eye budding, softwood cuttings, semi-hardwood cuttings, and hardwood cuttings. Asexual propagation techniques in in Le Cannet de Maures, Var, France, such as eye budding, softwood cuttings, semi-hardwood cuttings, and hardwood cuttings, have shown that the characteristics of the new plant variety are homogeneous, stable, and strictly transmissible by such asexual propagation from one generation to another. Accordingly, the new plant variety undergoes asexual propagation in a true-to-type manner.

SUMMARY OF THE INVENTION

It was found that the new variety of bedding rose plant of the present invention possesses the following combination of characteristics:

(a) forming yellow-colored blossoms,
(b) providing double flowers, and
(c) exhibiting a bushy and compact habit.

The new plant variety well meets the needs of the horticultural industry. It can be grown to advantage as ornamentation in parks, gardens, public areas, and residential landscapes. Accordingly, it is particularly well suited for growing in the landscape.

The new plant variety can be readily distinguished from its ancestors. More specifically, the new plant variety displays darker yellow flowers compared to the flowers of the 'KORgeleflo' variety (i.e., the seed parent). Additionally, the new plant variety exhibits a bushy and compact growth habit compared to the more upright growth habit of the unnamed seedling male parent (i.e., the pollen parent). Moreover, the new plant variety can be readily distinguished from non-parental related similar varieties. For example, the new plant variety has flowers with more petals compared to the 'SPRYLWKO' variety (not patented).

The new plant variety has been named the 'MEISAXA' variety.

BRIEF DESCRIPTION OF THE PHOTOGRAPH

The accompanying photograph shows, as nearly true as it is reasonably possible to make the same in a color illustration of this character, typical specimens of the plant parts of the new variety. The rose plants of the new variety were approximately three years of age and were observed during September while budded on its own roots and growing outdoors at Le Cannet des Maures, Var, France. Dimensions in centimeters are indicated at the bottom of the photograph.

Element 1—illustrates a specimen of a young shoot.

Element 2—illustrates a specimen of a floral bud before the opening of the sepals.

Element 3—illustrates a specimen of a floral bud at the opening of the sepals.

Element 4—illustrates a specimen of a floral bud at the opening of the petals.

Element 5—illustrates a specimen of a flower in the course of opening.

Element 6—illustrates a specimen of an open flower—plan view—obverse.

Element 7—illustrates a specimen of an open flower—plan view—reverse.

Element 8—illustrates a specimen of a fully open flower—plan view—obverse.

Element 9—illustrates a specimen of a fully open flower—plan view—reverse.

Element 10—illustrates a specimen of a floral receptacle showing arrangement of the stamens and pistils.

Element 11—illustrates a specimen of a floral receptacle showing arrangement of the pistils (stamens removed).

Element 12—illustrates a specimen of a flowering stem.

Element 13—illustrates a specimen of a leaf with 3 leaflets—plan view—upper surface.

Element 14—illustrates a specimen of a leaf with 5 leaflets—plan view—under surface.

Element 15—illustrates a specimen of a leaf with 7 leaflets—plan view—upper surface.

DETAILED BOTANICAL DESCRIPTION

The chart used in the identification of colors is that of The Royal Horticultural Society (The R.H.S. Colour Chart, 2015 edition). The terminology which precedes reference to the chart has been added to indicate the corresponding color in more common terms. The R.H.S. Colour Chart designation used herein represents the closest color observed on the majority of the specified botanical features. The description is based on a three-year-old specimen of the new plant variety, observed during September, while budded on its own roots and growing outdoors at Le Cannet des Maures, Var, France.

Botanical classification: *Rosa hybrida* cultivar 'MEISAXA'.

Commercial classification: Bedding Rose.

Plant:

*Habit*.—Bushy and compact.

*Height*.—Approximately 80.0 cm on average.

*Width*.—Approximately 90.0 cm on average.

Branches:

*Stem color*.—Old wood: Green Group 137B. — young stems: Yellow-Green Group 144A slightly suffused with anthocyanin coloration of Greyed-Orange Group 176A.

*Length*.—From the crown to the flower is typically between 30.0 cm to 60.0 cm.

*Diameter*.—Typically between 0.4 cm to 0.7 cm.

*Prickles*.—Configuration on adult stems: concave, elongated, and curved downwards on the upper surface and concave on the under surface. — quantity: approximately 6 prickles on average per 10 cm long young stem and approximately 10 prickles on average per 10 cm long adult stem. — length: typically between 0.5 cm to 0.7 cm on young stems and typically between 0.5 cm to 0.7 cm on adult stems. — length of the base: typically between 0.5 to 0.8 cm on young stems and typically between 0.4 to 0.8 cm on adult stems. — width at base: typically between 0.1 cm to 0.2 cm on young stems and typically between 0.1 cm to 0.3 cm on adult stems. — base shape: obovate, very narrow, and long on young stems; obovate, narrow, and medium on adult stems. — color on young stems: Greyed-Purple Group 187C. — color on adult stems: Yellow-Green Group 144C.

*Anthocyanin coloration of young shoots*.—Greyed-Red Group 178A.

*Internode numbers on entire branch*.—Typically between 10 to 15.

*Internode length*.—Typically between 2.5 cm to 5.0 cm.

Leaflets:

*Number*.—3, 7, and most often 5.

*Shape*.—Tip: acute. — base: rounded.

*Serration*.—Small and single.

*General appearance*.—Elliptical.

*Undulation*.—Weak.

*Glossiness of upper side*.—Medium.

*Texture*.—Soft.

*Smoothness*.—Upper surface: smooth. — under surface: smooth.

*Venation*.—Color is Green Group 138B; and pattern is imparipinnate.

*Size*.—Terminal leaflet: length is typically between 3.3 cm and 4.7 cm; width is typically between 2.2 cm and 2.8 cm. — 5-Leaflet leaf. length is typically between 8.0 cm and 10.5 cm; width is typically between 5.0 cm and 6.0 cm.

Foliage:

*General appearance*.—Rather dense with a semi-glossy aspect.

*Young foliage*.—Upper surface color: a color between Green Group 143A and Yellow-Green Group 144A. — under surface color: Yellow-Green Group 146D.

*Adult foliage*.—Upper surface color: Green Group 137A. — under surface color: Green Group 138B.

*Petiole*.—Texture: upper surface is smooth and glandular; under surface is smooth. — length: typically between 2.0 cm and 3.0 cm. — width: approximately 0.1 cm on average. — upper surface color: Green Group 137B. — under surface color: Yellow-Green Group 144A.

*Rachis*.—Rachis length of terminal leaflet: typically between 2.5 cm to 3.0 cm. — rachis width of terminal leaflet: approximately 0.1 cm on average. — texture: upper surface is smooth and few glandular; under surface is smooth with very few prickles (1 to 3). — upper surface color: Green Group 137B. — under surface color: Yellow-Green Group 144A.

*Stipules*.—Length: approximately 0.15 cm on average. — width: approximately 0.2 cm on average. — general appearance: narrow. — texture: smooth on upper and under surfaces. — upper surface color: Green Group 137A. — under surface color: Green Group 138B.

Inflorescence:

*Number of blossoms per stem*.—Typically 1 to 5 blooms per stem on average.

*Lastingness of the bloom*.—On the plant: approximately one week. — in vase: not tested.

*Bud*.—Shape: conical. — length: approximately 1.7 cm on average. — width: approximately 1.3 cm on average. — color as calyx breaks: upper surface: Yellow Group 9A with no basal spot. under surface: Yellow Group 12A with no basal spot.

*Sepals*.—Number: commonly 5 (sometimes 6). — length: typically between 2.0 cm and 2.7 cm. — width: typically between 0.6 cm and 0.9 cm. — shape: at the top: elongated and narrow (sometimes very elongated). at the base: flat at union with the receptacle. — extensions: typically 2 to 3 sepals with 1 or 2 extensions with a length typically between 0.2 cm and 0.8 cm and a width of approximately 0.1 cm on average. — upper surface: texture: tomentous. color: Yellow-Green Group 147C. — under surface: texture: smooth. color: Yellow-Green Group 144A slightly suffused with Greyed-Orange Group 176A.

*Receptacle*.—Color: Yellow-Green Group 144A. — length: approximately 0.5 cm on average. — width: approximately 0.6 cm on average. — surface: smooth. — shape: funnel shaped.

*Peduncle*.—Length: typically between 1.5 cm to 2.8 cm. — width: approximately 0.2 cm on average. — surface: smooth. — color: Yellow-Green Group 144A amply suffused with Greyed-Purple Group 185A.

*Flower*.—Diameter when open: typically between 7.0 cm to 8.0 cm. — depth of the flower: approximately 5.0 cm on average. — shape: umbrella. — shape when viewed from above: irregular rounded. — shape of the upper part of the flower profile: umbrella. — shape of the lower part of the flower profile: crumpled. — type: double. — number of petals under normal conditions: approximately 70 on average. — petals: shape: lanceolate (rounded and rarely cordiform at the top and attenuated at the base). texture: resistant. length: typically between 1.2 cm and 4.0 cm. width: typically between 0.9 cm and 3.5 cm. — undulation of the petal: medium. — reflexing of the petal: medium. — petal incision: absent to very weak. — petal arrangement: imbricated with rare petaloid-like deformed petals. — petal drop: petals drop off cleanly before drying. — fragrance: none. — discoloration of the flower: slow discoloration up to White Group 155A slightly suffused with Greyed-Purple Group 185C. — color when opening: basal spot on the upper surface: No visible basal spot. upper surface: Yellow Group 9A. basal spot on the under surface: No visible basal spot. under surface: Yellow Group 10A. — color of the open flower: basal spot on upper surface: Yellow Group 9A. upper surface: Yellow Group 8B. basal spot on under surface: No visible basal spot. under surface of the flower: Yellow Group 10A. — anthers: typically between 40 to 50, length is approximately 0.2 cm on average, width approximately 0.1 cm on average, coloration is Yellow-Orange Group 21A, and arrangement is regular around styles. — filaments: length is typically between 0.2 cm to 0.7 cm; and coloration is Yellow-Orange Group 17B. — styles: length is typically between 0.3 cm to 0.8 cm, coloration is Greyed-Purple Group 185A at the bottom and Greyed-Yellow Group 160A at the base, and number is approximately 65 on average. — stigmas: length is typically less than 0.1 cm and coloration is Yellow Group 11A. — pollen: abundant; color is Greyed-Orange Group 163B. — hips: length is approximately 1.7 cm on average; coloration is Yellow-Green Group 146B suffused with Greyed-Red Group 178B and shape is rounded.

Development:

*Blossoming*.—Very abundant and nearly continuous early in the season; typically, in bloom outdoors from May to November in Le Cannet de Maures, Var, France.

*Resistance to diseases*.—Excellent tolerance against black spot (*Diplocarpon rosae*) and rust (*Phragmidium* sp.).

*Hardiness*.—Tested up to USDA Zones 5 to 9.

The new 'MEISAXA' variety has not been observed under all possible environmental conditions to date. Accordingly, it is possible that the phenotypic expression may vary somewhat with changes in light intensity and duration, cultural practices, and other environmental conditions.

I claim:

1. A new and distinct variety of bedding rose plant named 'MEISAXA' characterized by the following combination of characteristics:

(a) forming yellow-colored blossoms, (b) providing double flowers, and (c) exhibiting a bushy and compact habit;

substantially as herein shown and described.

* * * * *

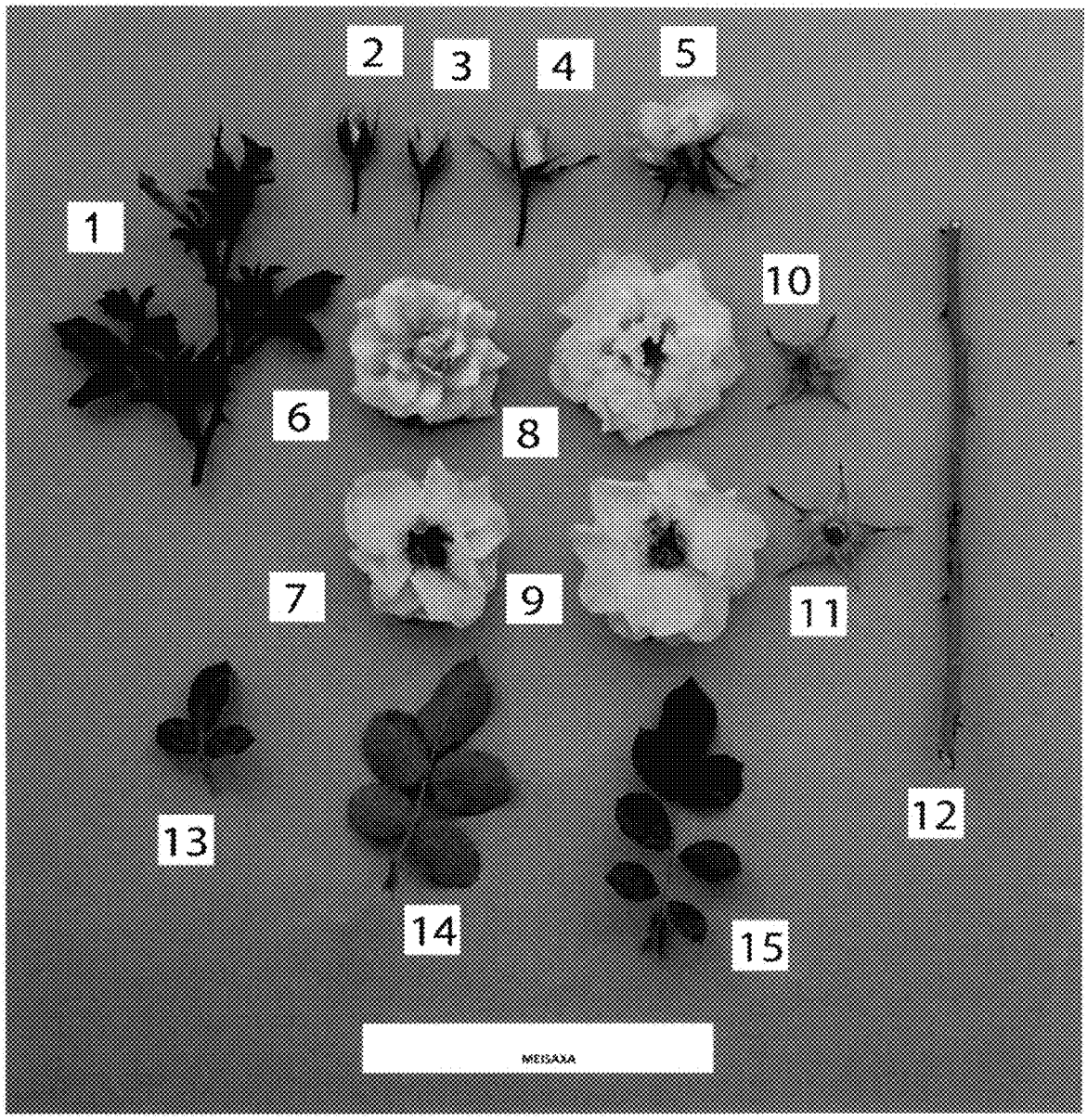
1
2
3
4
5
6
7
8
9
10
11
12
13
14
15
MEISAXA